(12) United States Patent
Lifshey

(10) Patent No.: US 6,544,213 B1
(45) Date of Patent: Apr. 8, 2003

(54) DUAL COMPARTMENT MIXING AND DISPENSING DEVICE

(75) Inventor: Arthur L. Lifshey, East Brunswick, NJ (US)

(73) Assignee: Merck & Co., Inc., Rahway, NJ (US)

( * ) Notice: Subject to any disclaimer, the term of this patent is extended or adjusted under 35 U.S.C. 154(b) by 372 days.

(21) Appl. No.: 09/659,221

(22) Filed: Sep. 11, 2000

(51) Int. Cl.⁷ .............................................. A61M 37/00
(52) U.S. Cl. .......................................... 604/89; 604/90
(58) Field of Search ............................ 604/82, 85, 87, 604/89, 90, 91, 191, 200, 232, 416

(56) References Cited

U.S. PATENT DOCUMENTS

| | | |
|---|---|---|
| 3,340,873 A | 9/1967 | Solowey |
| 3,354,883 A | 11/1967 | Southerland |
| 3,397,694 A | 8/1968 | Ogle |
| 3,411,503 A | 11/1968 | Santomieri |
| 4,330,531 A | 5/1982 | Alliger |
| 4,331,146 A | 5/1982 | Brignola |
| 4,412,836 A | 11/1983 | Brignola |
| 4,950,237 A | 8/1990 | Henault |
| 5,122,117 A * | 6/1992 | Haber et al. ................. 604/90 |
| 5,217,433 A | 6/1993 | Bunin |
| 5,472,422 A * | 12/1995 | Ljungquist ................. 604/89 |
| 5,630,800 A * | 5/1997 | Blank et al. ................. 604/90 |
| 5,637,100 A * | 6/1997 | Sudo ............................ 604/89 |

* cited by examiner

Primary Examiner—Anhtuan T. Nguyen
(74) Attorney, Agent, or Firm—James M. Hunter, Jr.; Mark R. Daniel

(57) ABSTRACT

The present invention is directed to a dual compartment, mixing and dispensing device suitable for the containment of two separate pharmaceutical components that mixable, upon breaking of a seal that separates the compartments, to provide an instantly mixed dose of medication. The medication can be administered to a patient through an aperture located at one end of the device. The device is characterized as two compartments connected by a flexible, sealed orifice, wherein the two components are separated. Flexing of the device at the orifice breaks the seal and allows mixing of the components to prepare the dose. Thereafter, an end-portion of the device can be opened for oral administration of the dose.

20 Claims, 5 Drawing Sheets

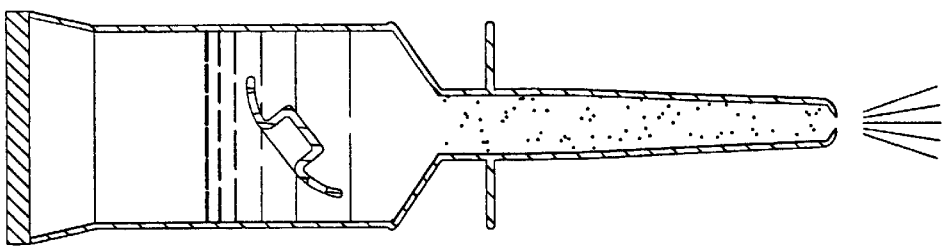
FIG. 4I
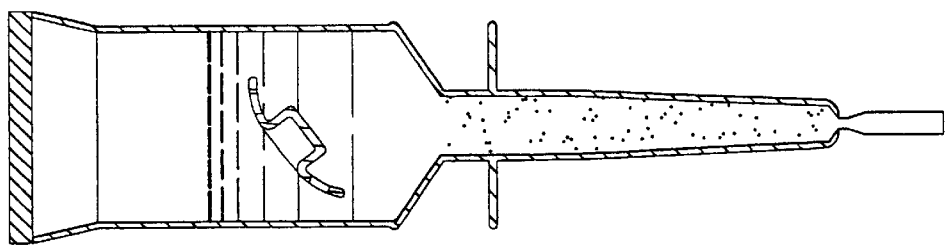
FIG. 4H
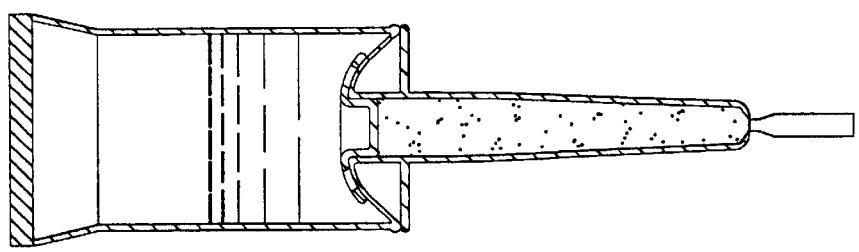
FIG. 4G

DUAL COMPARTMENT MIXING AND DISPENSING DEVICE

FIELD OF THE INVENTION

The invention relates to a dual compartment, mixing and dispensing device suitable for packaging and premixing pharmaceutical preparations just prior to direct administration to a patient.

BACKGROUND OF THE INVENTION

Due to degradation and formation of unwanted by-products, many two component pharmaceutical formulations must be stored separately prior to administration. Formulations characterized as two components, wherein the components must be pre-mixed in specified proportions prior to administration, i.e. in vitro mixing, are placed in separate containers for distribution. Prior to administration, exact amounts of each component must be pre-measured, combined, and mixed to provide a formulated dosage. Often these two-component preparations are not accurately measured or improperly mixed, and sometime multiple doses of pre-mixed formulation are stored for excess time. Typical of the two component preparations are oral vaccines and medications, opthalmic and nasal preparations, etc.

Prior art devices having multiple compartments for the separate containment of enclosed components for mixing prior to use are disclosed in U.S. Pat. Nos. 3,340,873, 3,354,883, 3,397,694, 3,411,503, 4,412,836, 4,330,531, 4,331,146, 4,950,237 and 5,217,433. These references disclose various novelties from mixing mechanisms to hydraulic pressure seal removing devices.

It is an objective of the present invention to provide a device for easily pre-mixing and administering a multi- or unit-dose of formulation just prior to the use thereof. Yet another objective of the invention is directed to processes for filling the device, and pre-mixing and dispensing a formulation from the device.

This and other objectives of the present invention will become apparent from the description and drawings herein.

SUMMARY OF THE INVENTION

The present invention is directed to a dual compartment, mixing and dispensing device suitable for containment and premixing of two separate components prior to administration to a patient, comprising:

a. first and second tubular-shaped compartments having open ends and walls for internal containment of first and second components, respectively, wherein the compartments are axially aligned;

b. an orifice connecting the first and second compartments together at an open end of each compartment along the axial alignment;

c. a transition wall on the second compartment at the orifice-second compartment interface comprising a reciprocally inverting conical-shape, concave wall, which funnels towards the orifice, and a continuous edge defined as the circumference of the second compartment leading to the conical-shape, concave wall, wherein the conical-shape, concave wall being perpendicular to the axially alignment of the compartments, said conical-shape, concave wall second compartment capable of inverting to a conical-shape, convex wall by forcing the first and second compartments towards each other along the axial alignment thereof;

d. closing means at the open end of the first compartment opposite the orifice to prevent flow of components therefrom;

e. a dish seal located inside the orifice being axially removable to the second compartment, the dish seal having first and second closed ends, the first end abutting the first compartment and the second end extending into the second compartment, the second end having a seal-pushing element attached thereto, wherein the dish seal prevents intermixing of the first and second components, and wherein the seal-pushing element moves perpendicular to the axial alignment;

f. a disc-shaped, flange element located on the exterior of the orifice at the orifice-first compartment interface, perpendicular to the axial alignment, wherein the diameter of the flange is proximal to the continuous edge of the transition wall of the second compartment; and g. sealing means at the open end of the second compartment opposite the orifice to prevent flow of the components therefrom, the first component being dispensed into the first compartment; the second compartment being reciprocally inverting along the axial alignment toward the first compartment to invert the conical-shape, concave wall to the conical-shape, convex wall so that the continuous edge of the second compartment contacts the flange element, wherein the concave-shape of the transition wall inverts to the convex-shape; the dish seal being placed in the orifice to contain the first component in the first compartment; a second component being dispensed into the second compartment; the second compartment being sealed to contain the second component, wherein forcing the compartments away from one another along the axial alignment at the orifice, causes the convex, transition wall to contact the seal-pushing element, thereby removing the dish seal from the orifice, wherein the conical-shape, convex wall inverts to a conical-shape, concave wall.

The dual compartment, mixing and dispensing device is useful for separate containment of two, pre-measured pharmaceutical components that a pre-mixable in the device immediately prior the direct administration to a patient. Upon flexing and pulling the compartments apart, the dish seal, which prevents flow of the two components to opposite compartments, is dislodged from the orifice allowing the components to readily mix in the compartments to provide a formulated multi- or unit-dose of medication. A multi-dose is defined as a formulation suitable for storage for about 30 days. After complete mixing of the components by way of diffusion or agitation of the device, the closing means can be removed from the first compartment to administer the formulated dose to a patient.

BRIEF DESCRIPTION OF THE DRAWINGS

FIG. 1A provides a top view in elevation of the disk seal and seal-pushing element;

FIGS. 4G–4I are a front view in elevation and section illustrating a process of mixing and opening the mixing and dispensing device.

DETAILED DESCRIPTION OF THE INVENTION

The invention described herein is a dual compartment, mixing and dispensing device suitable for pre-mixing and administrating a single unit of medication. The device can be used to directly administer a non-intramuscular/non-intravenous dose of a formulation to a patient.

Figure 1:
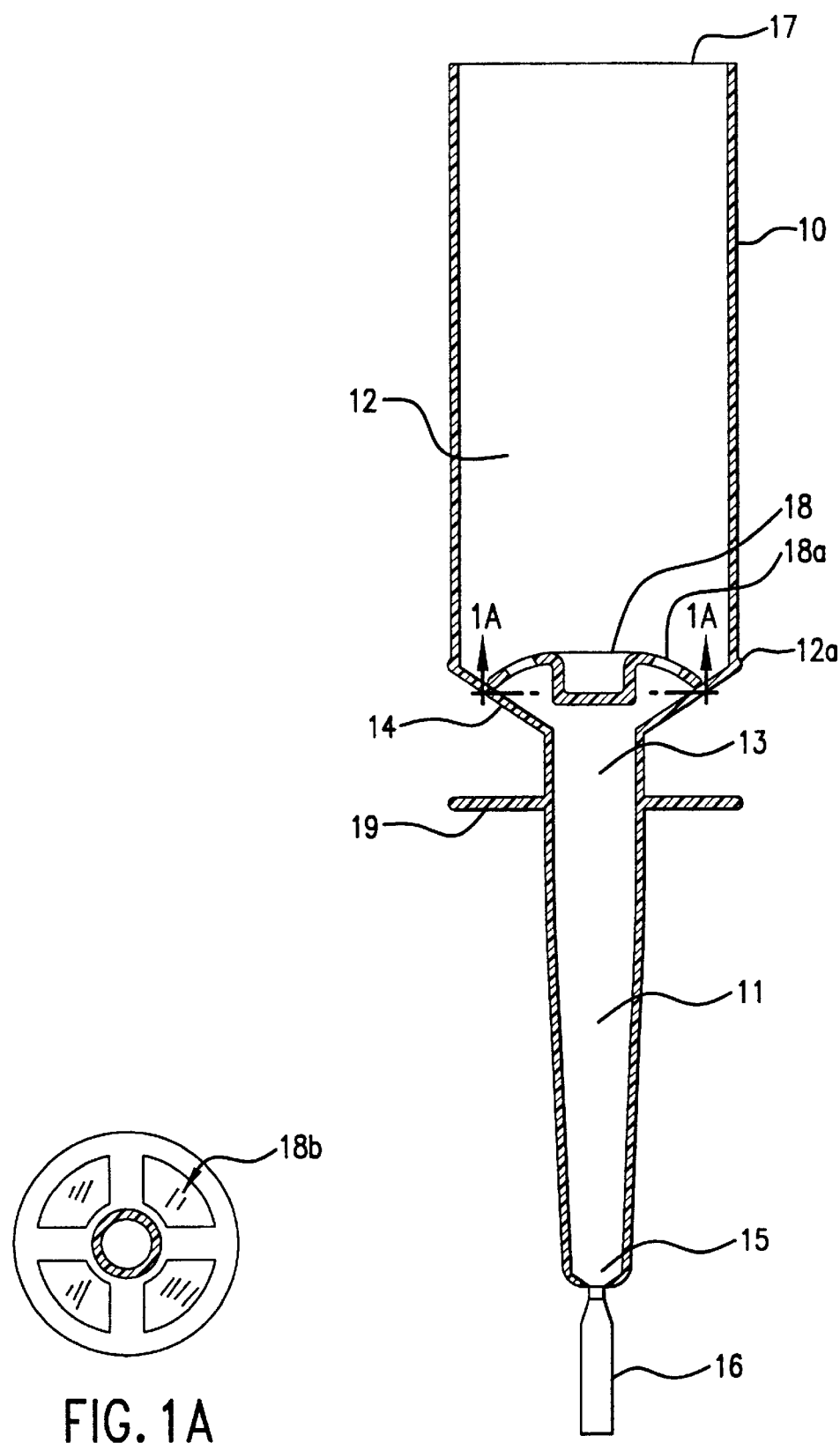
FIG. 1 is a front view in elevation and section of the mixing and dispensing device illustrating the dish seal member outside the orifice, wherein the conical wall of the second compartment is concave position.

Referring to FIG. 1, a typical embodiment of the dual compartment, mixing and dispensing device 10 is illustrated. The mixing and dispensing device is characterized as a first compartment 11 generally conforming to a tubular-shape for the containment of a first component, and a second compartment 12 conforming to a tubular-shape for the containment of a second component. The compartments are connected by orifice 13, wherein the orifice is axially aligned with the compartments. At the orifice-second compartment interface is a transition wall 14 conforming to a conical-shape, concave wall having a continuous edge 12a that converges inwardly towards the orifice. At the end of the first compartment, opposite the orifice is an opening 15 having closing means 16 for preventing discharge of the components from the device. At the end of the second compartment, opposite the orifice, is an opening 17 for filling the chambers, the opening being in axial alignment with the orifice. Positioned above the orifice in the second compartment is a dish seal 18 that plugs the first compartment to prevent migration of the first component to the second compartment, and migration from the second component to the first compartment. Seal-pushing element 18a, preferably having a concave disc surface, is attached to the dish seal Located at the orifice-first compartment interface is a flange element 19 that extends externally around the orifice to form a disc. FIG. 1A is a top view in detail of the seal disk 18 and seal-pushing element 18a, wherein four apertures or holes 18b appear in the surface of the seal-pushing element.

Figure 2:
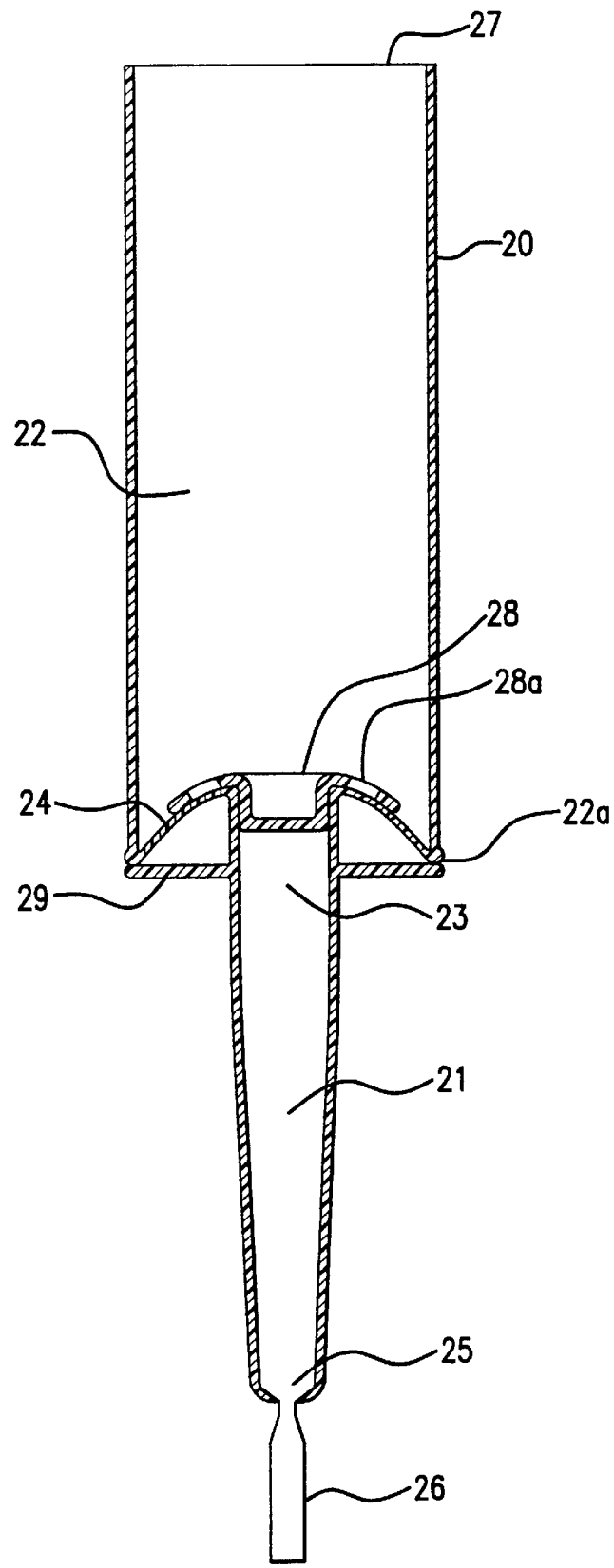
FIG. 2 is a front view in elevation and section of the mixing and dispensing device illustrating the disk seal member inside the orifice, wherein the conical wall of the second compartment is in a convex position.

FIG. 2 illustrates a device 20 having a first compartment 21 for containment of a first component, and a second compartment 22 for containment of a second component, wherein the first and second compartments are connected by an orifice 23 that is in axial alignment with the compartments. Mixing and dispensing device 20 is further characterized by an opening 25 at the end of the first compartment, opposite the orifice, in axial alignment therewith, and closing means 26 for preventing discharge of the components from the device. Opening 27, at the end of the second compartment, opposite the orifice, is suitable for filling the device with the components. Dish seal 28 having concave shape, seal-pushing element 28a is fixed into the orifice in a sealing position. Located at the orifice-first compartment interface is a flange element 29 that extends externally around the orifice to form a convex disc. The transition wall 14 of FIG. 1 having a conical-shape, concave surface 14 has been inverted into a conical-shape, convex surface 24 having continuous edge 22a that abuts flange element 29. Seal-pushing element 28a, having a convex-shape that conforms to the shape of the conical-shape, convex wall, is raised over the orifice. Applying an inward pushing force to the compartments, i.e. pushing the second compartment towards the first compartment along the axial alignment, the conical-surface, concave wall of the second compartment can be reciprocally inverted into a conical-shape, convex wall. Only when the second compartment is in a convex position, can the dish seal be installed in the orifice; since the seal-push that attached to the dish seal conforms to a concave shape. Generally, in this position the convex angles of the transition wall and seal-push 28a are parallel, and the continuous edge 22a abuts the flange element 29.

Figure 3C:
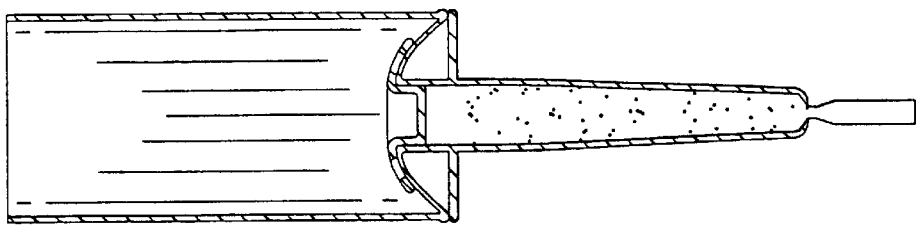
FIGS. 3A–3F are a front view in elevation and section illustrating a process of filling and assembling the mixing and dispensing device.
Figure 3B:
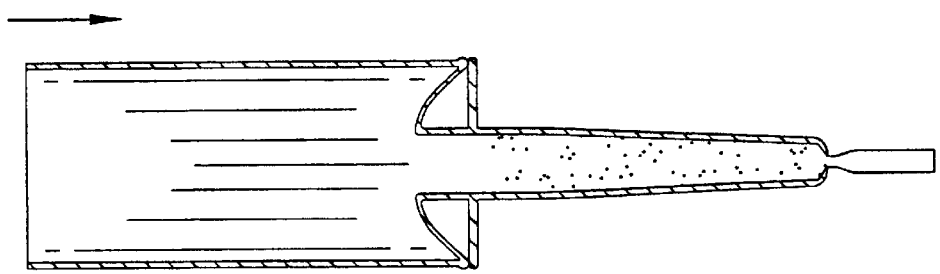
Figure 3A:
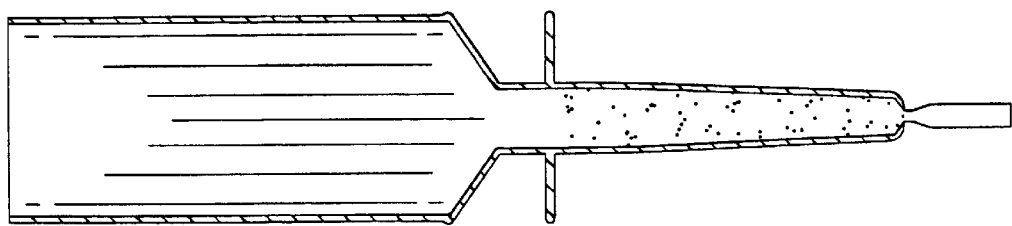
Figure 3F:
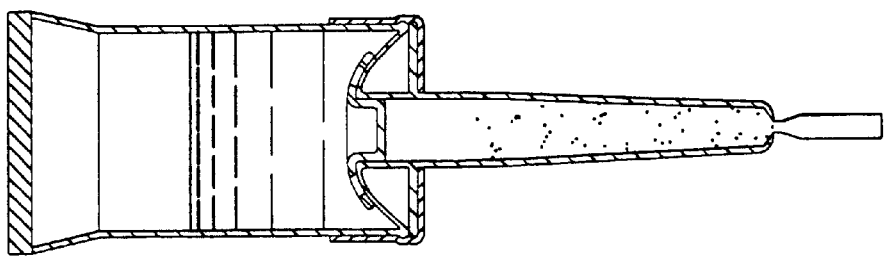
Figure 3E:
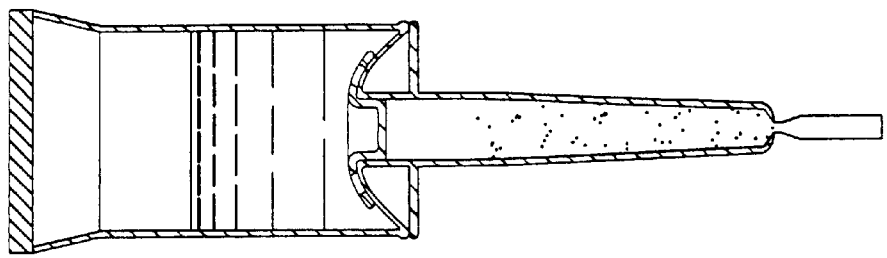
Figure 3D:
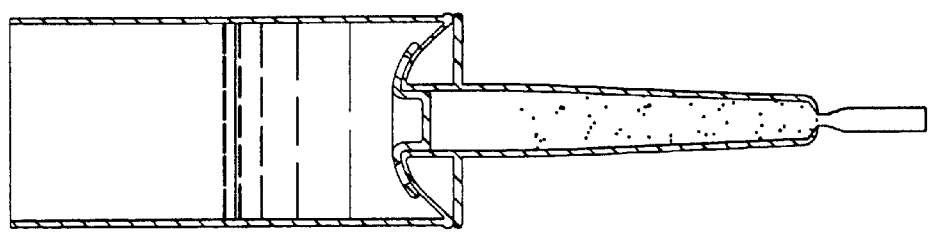

FIGS. 3A–3F illustrate a step-wise sequence of the process of filling the device with the first component, plugging the orifice with the dish seal, adding the second component, and sealing the second compartment. At sequence FIG. 3A, the device having been fabricated is shown in a stationary, inverted position, wherein the first compartment has been filled with the first component. At sequence FIG. 3B, a downward force having been applied to the transition wall of the device, the conical-shape, concave wall has been inverted to the conical-shape, convex wall. Optionally, the step-wise sequence of 3A and 3B can be interchanged, wherein the transitional wall of the second compartment can be inverted to a convex wall followed by filling the first compartment with a first component. Sequence FIG. 3C illustrates the device wherein the transition wall having been inverted to the convex wall, the first component being in the first compartment, and the convex-shaped, dish seal is placed in the orifice. At sequence FIG. 3D, the second component has been dispensed into the second compartment. Sequence FIG. 3E illustrates the final step of the process, wherein the mixing and dispensing device has been sealed at the opening of the second compartment. Optionally, sequence FIG. 3F illustrates a step where the mixing and dispensing device has a shrink band, safety seal applied to the area of the flange element and conical-shape, convex wall to further prevent the it from inverting to the conical-shape, concave wall.

FIGS. 4G–4I illustrates a step-wise sequence of the process of mixing the components to produce a multi- or unit-dose formulation, and removing the closure located at the aperture for administration of the formulation. Sequence FIG. 4G illustrates the mixing and dispensing device, the optional shrink band, safety seal having been previously removed, where a pulling and/or flexing force along the axial alignment is applied to the two compartments. Sequence FIG. 4H shows the device wherein the convex wall has inverted to a concave wall, and the dish seal has been dislodged from the orifice to facilitate mixing of the components by physical shaking or diffusion. Lastly, sequence FIG. 4I illustrated the mixing and dispensing device wherein the closing means has been removed from the aperture and the formulation is ready for administration to a patient.

The first compartment of the dual compartment mixing and dispensing device, which contains the first component, can be characterized as a tubular-shape nozzle having an opposed first open end suitable for dispensing a formulation, and a second open end suitable for attachment to an orifice, wherein the first and second open ends are perpendicular to the axial alignment of the nozzle. Closing means in the form of a twist-off plug or cap can be placed over the first open end of the nozzle to prevent loss of components therefrom. Typically, the nozzle diameter will gradually decrease at an angle of from about 80° to about 20° to form a cylindrical channel.

The second compartment of the device, which contains the second component, can be characterized as a tubular-shape vessel having opposed first and second open ends, wherein the first and second open ends are perpendicular to the axial alignment of the tube. The first end of the second compartment having a transition wall capable of reciprocally inverting between a conical-shape, concave wall and a conical-shape, convex wall, wherein the transition wall in perpendicular to the axial alignment of the compartment. The transition wall-second compartment interface has a continuous edge perpendicular to the axial alignment of the tube, wherein in the concave wall diameter decreases as the wall approaches the orifice. The second end of the second compartment being suitable for receiving the second component and a sealing means.

Generally, the orifice, which connects to the second open end of the first compartment and the first open end of the second compartments, is a tubular-shape channel in axial alignment with the first and second compartments. The orifice is generally of uniform diameter throughout its entire length and should be large enough to provide rapid mixing of the components. The length of the orifice should be sufficiently long to receive, retain and dislodge the dish seal as well as provide sufficient length, based on the diameter of the second compartment and the angle of concave transition wall, for reciprocally inverting the wall from concave to convex.

The dish seal will conform to the diameter, length and shape of the orifice to prevent flow of the components and facilitate easy removal from the orifice. As will become obvious to those in the art, optionally a gasket element can be fabricated into the dish seal to further prevent leakage between the compartments. When placed inside the orifice, the first end of the dish seal abuts the first compartment and the second end extends into the second compartment. The second end of the dish seal attaches to the seal-pushing element. The seal-pushing element protrudes into the second compartment and conforms to the shape of a convex disc, wherein the disc is perpendicular to the axial alignment of the first and second compartments, and the orifice. The seal-pushing element, optionally, can contain several holes or apertures in the surface. These holes are suitable for preventing the dish seal from remaining in the orifice during the process of dislodging, as well as reinsertion of the dish seal into the orifice during the process of mixing the two components. With the convex-shape disc attached thereto, the dish seal will snuggly fit inside the orifice only when the continuous edge of the transition wall is inverted to the conical-shape, convex wall. Preferably, the convex-shape, seal-pushing element of the dish seal and the conical-shape, convex wall will conform to identical shapes so that the seal-pushing element abuts and rests atop of the convex wall.

The flange element, located on the exterior surface of the orifice at the orifice-first compartment interface, is a disc of proximal diameter to the continuous edge of the second compartment leading to the orifice. The flange element is positioned perpendicular to the axial alignment of the first and second compartments, and the orifice. When the device is completely assembled and filled, the continuous edge of the conical-shape, convex wall will preferably abut against the flange element. In this position, the convex wall has inverted to completely cover the orifice from external view.

After the second compartment of the device is filled, a sealing means (in the form of a heating element for a thermoplastic, elastomeric material) can be placed around the opening of the compartment to close and seal the second open end of the second compartment. Optionally, a shrink wrap, safety seal or other suitable non-tamper mechanism can be placed over the flange element and abutting continuous edge, as well as the aperture and closing means of the first compartment to secure the device from tamper.

Generally, the mixing and dispensing device can be fabricated as one continuous unit from any flexible, elastic materials to ensure the reciprocating movement necessary for the transition wall to invert. Typically, the device can be fabricated from thermoplastic, elastomeric materials using molding processes known in the art. A preferred thermoplastic, material exhibiting good elasticity is low-density polyethylene, and a suitable manufacturing process is injection molding, wherein the first and second compartments, orifice, and flange element are molded as one continuous piece. After manufacturing, the device and component parts, i.e. dish seal and closing means, thereof can be assembled in accordance with the sequence of FIG. 3.

To use the device, the optional seal placed over the conical-shape, convex wall and flange element, and closing means is first removed. Holding the device in one hand at the second compartment with the other hand grasping the first compartment, the compartments are gently flexed and/or pulled apart. This force inverts the conical-shape, convex wall to the conical-shape, concave wall. The inverting wall dislodges the dish seal from the orifice, and the components can be pre-mixed by shaking the device. After complete mixing, the closing means can be removed from the first compartment, and the pre-mixed formulation dispensed by squeezing the second compartment.

I claim:

1. A dual compartment mixing and dispensing device suitable for containment and premixing of two separate components prior to administration to a patient, comprising:
   a. first and second tubular-shaped compartments having open ends and walls for internal containment of first and second components, respectively, wherein the compartments are axially aligned;
   b. an orifice connecting the first and second compartments together at an open end of each compartment along the axial alignment;
   c. a transition wall on the second compartment at the orifice-second compartment interface comprising a reciprocally inverting conical-shape, concave wall, which funnels towards the orifice, and a continuous edge defined as the circumference of the second compartment leading to the conical-shape, concave wall, wherein the conical-shape, concave wall being perpendicular to the axially alignment of the compartments, said conical-shape, concave wall second compartment capable of inverting to a conical-shape, convex wall by forcing the first and second compartments towards each other along the axial alignment thereof;
   d. closing means at the open end of the first compartment opposite the orifice to prevent flow of components therefrom;
   e. a dish seal located inside the orifice being axially removable to the second compartment, the dish seal having first and second closed ends, the first end abutting the first compartment and the second end extending into the second compartment, the second end having a seal-pushing element attached thereto, wherein the dish seal prevents intermixing of the first and second components, and wherein the seal-pushing element moves perpendicular to the axial alignment;
   f. a disc-shaped, flange element located on the exterior of the orifice at the orifice-first compartment interface, perpendicular to the axial alignment, wherein the diameter of the flange is proximal to the continuous edge of the transition wall of the second compartment; and
   g. sealing means at the open end of the second compartment opposite the orifice to prevent flow of the components therefrom, the first component being dispensed into the first compartment; the second compartment being reciprocally inverting along the axial alignment toward the first compartment to invert the conical-shape, concave wall to the conical-shape, convex wall so that the continuous edge of the second compartment contacts the flange element, wherein the concave-shape of the transition wall inverts to the convex-shape; the dish seal being placed in the orifice to contain the first component in the first compartment; a second component being dispensed into the second compartment; the second compartment being sealed to contain the second component, wherein forcing the compartments away from one another along the axial alignment at the orifice, causes the convex, transition wall to contact the seal-pushing element, thereby removing the dish seal from the orifice, wherein the conical-shape, convex wall inverts to a conical-shape, concave wall.

2. The device according to claim 1, wherein the first compartment is a nozzle and the closing means is selected from a plug and cap.

3. The device according to claim 2, wherein the orifice is an open channel having a diameter equal to or larger than the diameter of the first compartment, and a length suitable for receiving the dish seal.

4. The device according to claim 3, wherein the dish seal conforms to a conical-shape, convex wall, and a plurality of holes are located in the seal-pushing element.

5. The device according to claim 4, wherein the conical-shape, convex wall of the dish seal conforms to the shape and abuts the conical-shape, convex wall of the second compartment.

6. The device according to claim 5, wherein the dish seal is a cylindrical-shaped plug having a gasket which contacts the orifice to prevent component flow therethrough.

7. The device according to claim 6, wherein the diameter of the conical-shape, concave-wall of the second compartment is larger than the diameter of the seal-pushing element.

8. The device according to claim 7, wherein forcing the compartments away from each other along the axial alignment cause contact of the conical-shape, convex wall with the dish push element inverting the conical-shape, convex wall to the conical-shape, concave wall, wherein the disk seal is removed from the orifice causing the first and second component to mix.

9. The device according to claim 7, wherein the constructed material is a flexible, elastomeric material.

10. The device according to claim 8, wherein the flexible, elastomeric material is low-density polyethylene.

11. The device according to claim 9, wherein the first and second components are selected from the group of liquids and powders, wherein at least one component is a liquid.

12. A dual compartment, mixing and dispensing device suitable for premixing two separate pharmaceutical components to provide a unit dosage formulation prior direct administration to a patient, comprising:

a. a first compartment in the form of an elongated, tubular-shape nozzle having walls for the internal containment of a first component, the nozzle having a first, open end for the discharge of components, and a second, open end for the receipt of components;

b. a second compartment in the form of an elongated tube having walls for the internal containment of a second component, the tube having a first and second opening;

c. a transition wall on the second compartment at the orifice-second compartment interface comprising an inverting conical-shape, concave wall, concaving towards the orifice having a continuous edge defined as the circumference of the second compartment leading to the conical-shape, concave wall, the conical-shape, concave wall being perpendicular to the axially alignment, the conical-shape, concave wall capable of inverting to a conical-shape, convex wall by forcing the first and second compartments towards each other along the axial alignment thereof d. a tubular-shape orifice suitable for the passage therethrough of the first and second components having a first, open end connecting to the second end of the first compartment and a second open end connecting to the first end of the second compartment, wherein the openings of the first and second compartments, and the orifice are connected in axial alignment;

e. an aperture connected to the first end of the first compartment in axial alignment with the openings of the compartments and orifice, the aperture having removable closing means to prevent the discharge of components;

f. a dish seal, located inside the orifice, removable along the axial alignment to the second compartment, the dish seal having first and second closed ends, the first end abutting the first compartment and the second end extending into the second compartment, the second end having a convex-shape, seal-pushing element attached thereto, wherein the seal-pushing element is perpendicular to the axial alignment of the compartments, and wherein the dish seal conforms to and abuts the conical-shape, convex wall to prevents inversion of the convex wall to the concave wall; and g. sealing means at the opening of the second compartment opposite to the orifice to prevent flow of the components from the compartment, wherein the first component being dispensed into the first compartment; the second compartment being slideably moved toward the first compartment to provide a convex-shape surface on the second compartment so that the continuous edge of the second compartment contacts the flange element, wherein the concave-shape of the second compartment becomes a convex-shape; dish seal being placed in the orifice to contain of the first component in the first compartment, wherein the angle of the convex-shape surface and the angle of the seal-pushing element are about equivalent; a second component being dispensed into the second compartment; the second compartment being sealed to contain the second component, wherein sliding the compartments away from one another and flexing the device at the orifice, causes the convex-shape surface to contact the seal-pushing element, removing the dish seal from the orifice, wherein the convex-shape surface to become a concave-shape surface, wherein the first component to migrate to the second compartment and the second component to migrate to the first compartment thereby mixing the components to provide a dose, and thereafter removing the closing means from the aperture to dispense the dose.

13. The device according to claim 12, wherein the closing means is selected from the group consisting of removable caps and plugs.

14. The device according to claim 13, wherein the nozzle converges at an angle of from about 20° to about 80°.

15. The device according to claim 14, wherein the mixing and dispensing device is constructed from a thermoplastic, elastomeric material.

16. The device according to claim 15, wherein the thermoplastic, elastomeric material is low, density polyethylene.

17. The device according to claim 16, wherein the closing means is a heat seal.

18. The device according to claim 17, wherein the mixing and dispensing device is of a continuous, one piece construction.

19. The device according to claim 18, wherein the first component is selected form the group of powders and liquids.

20. The device according to claim 19, wherein the second component is a liquid.

* * * * *